United States Patent [19]

Belman

[11] 4,301,810
[45] Nov. 24, 1981

[54] VENTILATORY MUSCLE TRAINING APPARATUS

[75] Inventor: Michael J. Belman, West Covina, Calif.

[73] Assignee: City of Hope National Medical Center, Duarte, Calif.

[21] Appl. No.: 125,837

[22] Filed: Feb. 29, 1980

[51] Int. Cl.³ ............................................. A61M 15/00
[52] U.S. Cl. .................................... 128/720; 128/914; 128/207.16; 128/200.24; 272/99
[58] Field of Search ........... 128/716, 720, 725, 200.24, 128/203.25, 203.28, , 205.17, 205.11, 205.12, 204.18, 203.12, 727, 728, 730, 207.14, 726, 204.26, 207.12, 910, 207.16, 914; 272/99

[56] References Cited

U.S. PATENT DOCUMENTS

| | | | |
|---|---|---|---|
| 1,044,367 | 11/1912 | Evans | 272/99 X |
| 3,426,745 | 2/1969 | Farr | 128/730 |
| 3,513,843 | 5/1970 | Exler | 128/203.25 |
| 3,695,608 | 10/1972 | Hanson | 128/725 |
| 4,051,843 | 10/1977 | Franetzki | 128/720 |
| 4,086,923 | 5/1978 | Henkin | 128/205.11 |
| 4,143,872 | 3/1979 | Hanstad et al. | 272/99 R |

OTHER PUBLICATIONS

Leith et al., "Ventilatory Muscle Strength and Endurance Training", Oct. 1976, Journal of Applied Physiology, vol. 4, No. 4, pp. 508–516.

*Primary Examiner*—Henry J. Recla
*Attorney, Agent, or Firm*—Edward D. O'Brian

[57] ABSTRACT

A ventilatory muscle training apparatus is disclosed which utilizes a gas rebreathing system having a reservoir and a mouthpiece for use in conveying gas into and out of the reservoir during inhalation and exhalation. An adjustable valve-like aperture is located in the system in a position to vent some expired gas to the ambient atmosphere during exhalation and in a position such that some ambient air is drawn into the system from the ambient during inhalation. This aperture structure is capable of being adjusted so as to normalize the carbon dioxide content of the gas breathed in during inhalation to a patient's normal respiratory level. The reservoir used is preferably an enclosed chamber which is open to the ambient air remote from the mouthpiece. The apparatus also includes a means for use in monitoring the air flow through the mouthpiece so that the patient can determine that his or her breathing is in accordance with the intended manner of use of the apparatus.

16 Claims, 2 Drawing Figures

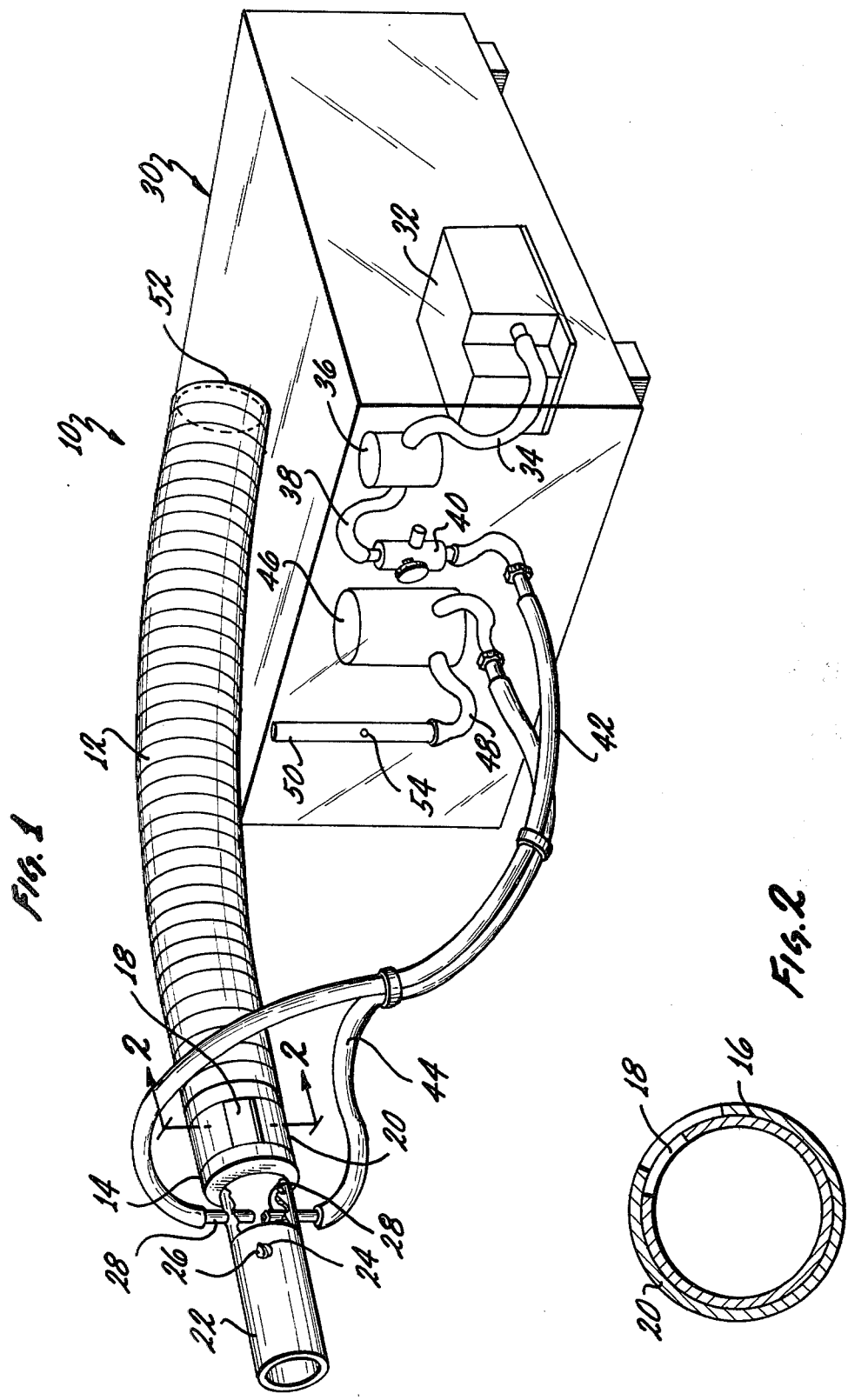

VENTILATORY MUSCLE TRAINING APPARATUS

BACKGROUND OF THE INVENTION

The invention set forth in this specification pertains to a new and improved ventilatory muscle training apparatus.

At this time it is considered the ventilatory muscle strength or endurance can be increased significantly by ventilatory muscle endurance training. Although this can be important in virtually any circumstance in which ventilatory muscle fatigue can limit the performance of an individual during exercise it is considered that this is of particular importance in connection with individuals suffering from chronic obstructive pulmonary disease. It is believed that it has now been established that ventilatory muscle training improves the ventilatory muscle performance of such individuals.

In the past several different types of closely related apparatuses have been proposed for use in ventilatory muscle training. It is not considered that an understanding of the present invention requires a detailed discussion of the construction of such prior apparatuses. In general they can be characterized as relatively complex and relatively difficult to adjust and use. Further, it is considered that they have been of such a character as to make it comparatively difficult for an individual such as a patient to monitor his or her use of such an apparatus to make certain that the apparatus is being used in the desired manner.

BRIEF SUMMARY OF THE INVENTION

The invention set forth in this specification is intended to provide a new and improved ventilatory muscle training apparatus which overcomes various objectionable aspects of prior apparatuses for ventilatory muscle training as are briefly indicated in a generalized manner in the preceding discussion. A new ventilatory muscle training apparatus of the invention is believed to be advantageous because it can be constructed at a lower cost than prior related apparatuses; because it may be easily and conveniently used with minimal difficulty; because it is quite reliable as a result of its simplicity; and because it is of such a character than an individual can easily monitor his or her use of the apparatus so as to determine that the apparatus is being utilized correctly or in a desired manner.

In accordance with this invention these and various other objectives are achieved by providing a ventilatory muscle training apparatus including a gas rebreathing system having a reservoir and a mouthpiece for use by an individual in conveying gas into and out of said reservoir during inhalation and exhalation and a gas content control means for venting some exhaled gas to the ambient during the use of said rebreathing system and for supplying some makeup ambient air to said rebreathing system during inhalation so that the gas inhaled through said mouthpiece has a carbon dioxide content within the physiological limits of the individual using said system which approximate the patient's normal mixed expired carbon dioxide level in which the improvement comprises:

said reservoir is substantially incapable of providing any resistance to the exhalation of gas through said mouthpiece into said reservoir, and said gas content control means comprises aperture means located within said system in a position in which some of the expired gas during exhalation is vented to the ambient and in which some ambient air is drawn into said system so as to be inhaled through the use of said mouthpiece along with gas from within said reservoir.

BRIEF DESCRIPTION OF THE DRAWING

Because of the nature of the invention it is considered that it is best more fully described with reference to the accompanying drawing in which:

FIG. 1 is an isometric view showing a presently preferred embodiment or form of an apparatus in accordance with this invention;

FIG. 2 is a partial cross-sectional view taken at line 2—2 of FIG. 1 illustrating the nature of the adjustable aperture or valve utilized in the apparatus indicated in FIG. 1.

It is believed that it will be apparent to those familiar with the application of mechanical principles to apparatuses utilized in the treatment of respiratory ailments that various different changes or modifications may be made in the precise apparatus illustrated without departing from the concepts or principles of the invention defined in the appended claims through the use of what is considered to be routine skill as is normally possessed by such individuals. For this reason the present invention is not to be considered as being limited to an apparatus constructed exactly as the illustrated apparatus.

DETAILED DESCRIPTION

In the drawing there is shown a ventilatory muscle training apparatus 10 of the present invention. It is considered that an understanding of this apparatus 10 is most easily conveyed by separately describing the various parts of it and then by indicating the functions of these parts as the apparatus 10 is used. This apparatus 10 utilizes an elongated, flexible tubular reservoir 12. This reservoir 12 is preferably at least twice the lung capacity of an individual who may use the apparatus 10 so that it can effectively serve its function as hereinafter indicated.

A nonflexible generally cylindrical end cap 14 is secured to one end (not separately numbered) of the reservoir 12 in any convenient manner. This end cap 14 is provided with a peripheral comparatively flat groove 16 in which there is located an aperture 18 which, in effect, leads into the interior of the reservoir 12. A small collar 20 fits within this groove 16 so that its position relative to the aperture 18 may be adjusted in order to vary the effective size of the aperture 18. This collar 20 is normally retained in any position in which it is located by frictional engagement with the cap 14 within the groove 16. In effect the structure involving the groove 16, the aperture 18 and the collar 20 constitutes a valve or valve means which can be adjusted as the apparatus 10 is set up for use.

The end cap 14 also holds a comparatively small tubular mouthpiece 22 which is adapted to be held within the mouth of an individual using the apparatus 10 in the intended manner. This mouthpiece 22 is sufficiently long so that when it is held by such an individual a small hole 24 in it will not be covered. During the normal use of the apparatus 10 this hole 24 may be, but is not necessarily, covered by a closure 26 such as a small stopper. The mouthpiece 22 also holds two aligned nozzles 28 constituting or serving as a fluidic type air jet amplifier. These nozzles 28 extend from the exterior of the mouthpiece 22 to the interior of this mouthpiece 22 and are spaced from one another a comparatively small amount as indicated in FIG. 1.

The apparatus 10 preferably also includes a small housing 30 containing a conventional air pump 32 which supplies air through a tube 34 to an accumulator 36 serving as a surge tank to minimize any effect of air being provided by the pump 32 at different pressures at different time intervals. Air from the accumulator 36 is supplied through another tube 38 to a conventional air flow control valve 40 capable of being used to adjust the air flow past this valve 40. The valve 40 is in turn connected to one of the nozzles 28 by another tube 42. The other of the nozzles 28 is connected by a further tube 44 to another accumulator 46. This further accumulator 46 is in turn connected by a tube 48 to a conventional flow measuring device 50—preferably a conventional rotometer.

During the use of the apparatus 10 an individual is instructed to both inhale and exhale through the use of the mouthpiece 22. During such initial use it is substantially immaterial as to whether or not the air pump 32 is operated so as to supply air to one of the nozzles 28. It is considered, however, that it is desirable to have this air pump 32 operating with the valve 40 open so as to permit a volume of air flow which will reasonably approximate the air flow desired during the intended use of the apparatus 10. When air is supplied to a nozzle 28 the flow of inhaled and expired gas relative to the nozzles 28 during inhalation and exhalation will not result in the introduction into the "system" (not separately numbered) including the reservoir 12 and the mouthpiece 22 of any significant amount of ambient air. This avoids possible interference with the accuracy of subsequent measurements and setting of the collar 20 relative to the aperture 18 as subsequently indicated.

In connection with this it will, of course, be realized that since the two nozzles 28 serve as an air jet amplifier that in the absence of flow generally traverse to a line between these two nozzles 28 that substantially all of the air emitted from one nozzle 28 will pass to the other of the nozzles 28. During such gas flow traverse to such a line between the two nozzles 28 some of the air passing from one of the nozzles 28 will not reach the other of the nozzles 28. Generally speaking the amount of such air from one of the nozzles 28 affected by such traverse gas flow so as not to reach the other of the nozzles 28 will be sufficiently small so that it is normally substantially insignificant.

The initial cycles of exhalation and inhalation through the mouthpiece 22 will result in expired gas replacing normal air within the reservoir 12. In order to minimize a possible pressure buildup within the reservoir 12 and to provide for venting of such air which is displaced with expired gas it is preferred to have the end 52 of the reservoir 12 remote from the mouthpiece 22 open to the ambient air. This end 52 should be sufficiently large so as to provide substantially no interference with gas flow. Because of its volume and elongated configuration there is little danger of ambient air mixing or flowing with expired air within the reservoir 12 to any significant extent as an individual inhales or exhales during the use of the apparatus 10.

Further, because the reservoir 12 is vented to the ambient atmosphere through the open end 52 so as to interfere with normal breathing to a minimal extent during such inhalation and exhalation comparatively little expired gas will move through the aperture 18 and very little ambient air will enter the "system" consisting of the mouthpiece 22 and the reservoir 12 through this aperture 18. This is particularly the case since the aperture 18 is located on the end cap 14 generally off to one side (not separately numbered) of the reservoir 12 somewhat away from the main path of flow of expired gas into and out of the mouthpiece 22. After the initial use of the apparatus 10 as described in the preceding a small sampling probe such as a tube (not shown) is normally inserted through the hole 24 so that an appropriate conventional gas analyzer (not shown) may be utilized to determine the normal carbon dioxide content of the gas exhaled by the user. As measurements to determine such content are made the collar 20 is adjusted relative to the aperture 18 so that sufficient exhaled gas escapes to the ambient atmosphere and so that sufficient ambient air is drawn in through the aperture 18 during exhalation and inhalation, respectively, so that the carbon dioxide content of the inhaled and exhaled air remains substantially constant. Normally this carbon dioxide content will correspond to the carbon dioxide content of the exhaled gas breathed out by a patient although at times a physician may wish to either increase or decrease this carbon dioxide of the inhaled gas content from this value.

After the aperture 18 has been "set" as indicated in the preceding the valve 40 will normally be adjusted so as to bias the rotor 54 in the rotometer 50 so as to indicate what may be referred to as a desired breathing level. In effect such a breathing level has two primary components—the role of inhalation and exhalation and the volume of gas moved into and out of the lungs during breathing. Such adjustment of the valve 40 will regulate the amount of air flowing through one of the nozzles 28 toward the other of the nozzles 28. The amount of such air reaching the other nozzle 28 will be determined by the air flow traverse to the small space between these two nozzles 28. The amount of air passing through one of the nozzles 28 to the rotometer 50 will, of course, be of primary concern in connection with the setting of the rotometer 50. This amount of air is, of course, variable in accordance with gas flow generally through the mouthpiece 22 and generally traverse to a line between the two nozzles 28.

After the position of the rotor 54 has been adjusted an individual utilizing the apparatus 10 will be able to tell by visual inspection of the rotor 54 if either he or she is breathing in accordance with the initial setting of the rotor 54. If the rotor 54 is above the initial setting the individual is either breathing too rapidly or is inhaling or exhaling more than an intended volume of gas, or both. If on the other hand the individual is breathing either too slowly and/or is inhaling or exhaling less than an intended volume of gas the rotor 54 will be below the position in which it has been set.

It is considered that it will be obvious from the preceding discussion that the nozzles 28 in association with the air pump 32 and the rotometer 50 and various other parts as described constitute a gas flow measurement apparatus or means. A wide variety of other different flow measuring devices can be utilized in accordance with the broad generic concepts of the present invention so as to provide various indications to an individual indicating whether or not such an individual is or is not breathing in a desired manner. Such a signal may take the form of a meter reading, the actuation of one or more light bulbs, or even the form of an audio signal which varies in accordance with the individual's breathing.

The particular flow measurement apparatus described is considered to be preferable for use with the present invention for several reasons. It is both simple and effective. Further, the flow measuring apparatus indicated is of such a character as not to significantly affect the operation of the remainder of the apparatus 10.

Obviously the construction of the precise apparatus 10 described can be varied to a reasonable extent. Thus, if the various tubes 42, 44 and 48 described are of a sufficiently large diameter or are sufficiently elastic in character it is unnecessary to utilize the accumulators 36 and 46 because these tubes will adequately function as these accumulators. Various changes of this type are considered to be within the scope of routine engineering skill. Although moisture condensation is not considered to be a significant problem in connection with this apparatus 10, if desired appropriate conventional collectors may be utilized to handle any moisture which may accumulate in the reservoir 12 or the end cap 14 during the use of the apparatus 10.

I claim:

1. A ventilatory muscle training apparatus including a gas rebreathing system having a reservoir means and a mouthpiece connected to said reservoir means for use by an individual in conveying gas into and out of said reservoir means during inhalation and exhalation and a gas content control means for venting some exhaled gas from said rebreathing system to the ambient during the use of said rebreathing system and for supplying some makeup ambient air to said rebreathing system during inhalation so that the gas inhaled through said mouthpiece has a carbon dioxide content within the physiological limits of the individual using said system which approximate the patient's normal mixed expired carbon dioxide level in which the improvement comprises:
said reservoir means being larger than the lung capacity of a user and being substantially incapable of providing any resistance to the exhalation of gas through said mouthpiece into said reservoir means, said reservoir means comprising an elongated, flexible, hollow tube, one end of said tube being connected to said mouthpiece, the other end of said tube being open to the ambient atmosphere, and
said gas content control means comprises an adjustable aperture means located within said system sufficiently adjacent to said mouthpiece so that some of the expired gas during exhalation is vented to the ambient and so that some ambient air is drawn into said system through said aperture means so as to be inhaled through the use of said mouthpiece along with gas from within said reservoir means.

2. A ventilatory muscle training apparatus as claimed in claim 1 wherein:
said reservoir means is an enclosed chamber which has an opening to the ambient atmosphere at a point sufficiently far from said mouthpiece so that there is substantially no danger of any significant ambient air passing through said chamber from said opening so as to be breathed during the use of said apparatus, said chamber being larger than the lung capacity of a user of said apparatus.

3. A ventilatory muscle training apparatus as claimed in claim 1 wherein:
said adjustable aperture means includes an aperture located so as to connect the interior of said system with the exterior of said apparatus generally between said mouthpiece and said reservoir means and a movable member capable of being moved in varying the effective size of said aperture.

4. A ventilatory muscle training apparatus as claimed in claim 1 including:
gas flow measurement means for measuring gas flow through said mouthpiece during inhalation and exhalation, said gas flow measurement means including indicating means for indicating whether or not said apparatus is being utilized at a desired breathing level.

5. A ventilatory muscle training apparatus as claimed in claim 1 including:
jet amplifier means responsive to gas flow through said mouthpiece located so as to measure flow through said mouthpiece, said jet amplifier means including indicating means for indicating the gas flow through said mouthpiece.

6. A ventilatory muscle training apparatus as claimed in claim 5 wherein:
said indicating means comprises a flow meter capable of being visually inspected so as to indicate the gas flow through said mouthpiece.

7. A ventilatory muscle training apparatus as claimed in claim 1 wherein:
the interior volume of said tube is at least twice the lung capacity of a user of said apparatus,
said mouthpiece is connected to said end cap so as to extend therefrom outwardly from said tube,
said adjustable aperture means includes an aperture located in said end cap and a collar located on said end cap so as to be capable of being moved relative to said aperture in order to control the effective area of said aperture,
jet amplifier means responsive to gas flow through said mouthpiece located within said mouthpiece in a position in which said jet amplifier means is capable of measuring gas flow through said mouthpiece,
said jet amplifier means including a flow meter remote from said mouthpiece for visually indicating gas flow through said mouthpiece,
said jet amplifier means also including an air source means for supplying air to operate said jet amplifier means and valve means for regulating the amount of air supplied to said jet amplifier means by said air source means.

8. A ventilatory muscle training apparatus as claimed in claim 7 wherein:
said adjustable aperture means is located on said end cap remote from said mouthpiece so as to be spaced from the principal gas flow into and out of said mouthpiece.

9. A ventilatory muscle training apparatus including a gas rebreathing system having a reservoir means and a mouthpiece connected to said reservoir means for use by an individual in conveying gas into and out of said reservoir means during inhalation and exhalation and a gas content control means for venting some exhaled gas from said rebreathing system to the ambient during the use of said rebreathing system and for supplying some makeup ambient air to said rebreathing system during inhalation so that the gas inhaled through said mouthpiece has a carbon dioxide content within the physiological limits of the individual using said system which approximate the patient's normal mixed expired carbon dioxide level in which the improvement comprises:

said reservoir means being larger than the lung capacity of a user and being substantially incapable of providing any resistance to the exhalation of gas through said mouthpiece into said reservoir means, said gas content control means comprises an adjustable aperture means located within said system sufficiently adjacent to said mouthpiece so that some of the expired gas during exhalation is vented to the ambient and so that some ambient air is drawn into said system through said aperture means so as to be inhaled through the use of said mouthpiece along with gas from within said reservoir means, and gas flow measurement means for measuring gas flow through said mouthpiece during inhalation and exhalation, said gas flow measurement means including indicating means for indicating whether or not said apparatus is being utilized at a desired breathing level.

10. A ventilatory muscle training apparatus as claimed in claim 9 wherein:

said reservoir means is an enclosed chamber which has an opening to the ambient atmosphere at a point sufficiently far from said mouthpiece so that there is substantially no danger of any significant ambient air passing through said chamber from said opening so as to be breathed during the use of said apparatus, said chamber being larger than the lung capacity of a user of said apparatus.

11. A ventilatory muscle training apparatus as claimed in claim 9 wherein:

said reservoir means comprises an elongated, flexible, hollow tube, one end of said tube being connected to said mouthpiece, the other end of said tube being open to the ambient atmosphere.

12. A ventilatory muscle training apparatus as claimed in claims 9 or 11 wherein:

said adjustable aperture means includes an aperture located so as to connect the interior of said system with the exterior of said apparatus generally between said mouthpiece and said reservoir means and a movable member capable of being moved in varying the effective size of said aperture.

13. A ventilatory muscle training apparatus as claimed in claim 9 and 11 including:

jet amplifier means responsive to gas flow through said mouthpiece located so as to measure flow through said mouthpiece, said jet amplifier means including indicating means for indicating the gas flow through said mouthpiece.

14. A ventilatory muscle training apparatus as claimed in claim 9 including:

jet amplifier means responsive to gas flow through said mouthpiece located so as to measure flow through said mouthpiece, said jet amplifier means including indicating means for indicating the gas flow through said mouthpiece, said indicating means comprising a flow meter capable of being visually inspected so as to indicate the gas flow through said mouthpiece.

15. A ventilatory muscle training apparatus as claimed in claim 9 wherein:

said reservoir means comprises an elongated, flexible, hollow tube, and an end cap at one end of said tube, the other end of said tube being open to the ambient atmosphere, the interior volume of said tube being at least twice the lung capacity of a user of said apparatus, said mouthpiece is connected to said end cap so as to extend therefrom outwardly from said tube, said adjustable aperture means includes an aperture located in said end cap and a collar located on said end cap so as to be capable of being moved relative to said aperture in order to control the effective area of said aperture, jet amplifier means responsive to gas flow through said mouthpiece located within said mouthpiece in a position in which said jet amplifer means is capable of measuring gas flow through said mouthpiece, said jet amplifier means including a flow meter remote from said mouthpiece for visually indicating gas flow through said mouthpiece, said jet amplifier means also including an air source means for supplying air to operate said jet amplifier means and valve means for regulating the amount of air supplied to said jet amplifier means by said air source means.

16. A ventilatory muscle training apparatus as claimed in claim 15 wherein:

said adjustable aperture means is located on said end cap remote from said mouthpiece so as to be spaced from the principal gas flow into and out of said mouthpiece.

* * * * *